US012203668B2

(12) United States Patent
Avasthi (10) Patent No.: US 12,203,668 B2
(45) Date of Patent: Jan. 21, 2025

(54) AIR QUALITY MONITORING DEVICE AND ASSOCIATED METHOD OF MANUFACTURING (71) Applicant: Honeywell International Inc., Charlotte, NC (US)

(72) Inventor: Rahul Avasthi, Allen, TX (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

(21) Appl. No.: 17/822,857

(22) Filed: Aug. 29, 2022

(65) Prior Publication Data

US 2024/0068684 A1    Feb. 29, 2024

(51) Int. Cl.
| *F24F 11/30* | (2018.01) |
| *F24F 110/10* | (2018.01) |
| *F24F 110/20* | (2018.01) |
| *F24F 110/64* | (2018.01) |
| *F24F 110/66* | (2018.01) |

(52) U.S. Cl.
CPC ........... *F24F 11/30* (2018.01); *F24F 2110/10* (2018.01); *F24F 2110/20* (2018.01); *F24F 2110/64* (2018.01); *F24F 2110/66* (2018.01)

(58) Field of Classification Search
None
See application file for complete search history.

(56) References Cited

U.S. PATENT DOCUMENTS

| 6,085,576 A | 7/2000 | Sunshine et al. |
| 6,266,995 B1 | 7/2001 | Scott |
| 7,165,547 B2 | 1/2007 | Truitt et al. |
| (Continued) | | |

FOREIGN PATENT DOCUMENTS

| AU | 2011356176 A1 | 7/2013 |
| EP | 2017586 A1 | 1/2009 |
| (Continued) | | |

OTHER PUBLICATIONS

Daniel Yee et al., U.S. Appl. No. 18/171,280 for "Air Quality Monitoring Device and Associated Method of Monitoring Air Quality", filed Feb. 17, 2023.

(Continued)

*Primary Examiner* — Thomas S McCormack
(74) *Attorney, Agent, or Firm* — ALSTON & BIRD LLP (57) ABSTRACT

An air quality monitoring device and an associated method of manufacturing. An example air quality monitoring device may include a housing having a chamber and an inlet port. The inlet port may be structured to receive an air flow from outside the housing and provide the air flow to the chamber. The air quality monitoring device may include a plurality of sensors disposed within the chamber and configured to measure air quality data associated with the air flow. The air quality monitoring device may include an adapter configured to be connected to the inlet port and a continuous positive airway pressure machine. The inlet port may be configured to receive the air flow from the continuous positive airway pressure machine via the adapter. The air quality monitoring device may include a controller connected with the plurality of sensors and configured to transmit the air quality data to a computing device.

14 Claims, 6 Drawing Sheets

(56) References Cited

U.S. PATENT DOCUMENTS

| | | | |
|---|---|---|---|
| 9,839,726 | B2 | 12/2017 | Ehlert |
| 10,695,516 | B2 | 6/2020 | Chaturvedi et al. |
| 11,045,800 | B1 | 6/2021 | Kaplan et al. |
| 2007/0068530 | A1 | 3/2007 | Pacey |
| 2009/0020120 | A1* | 1/2009 | Schatzl ................ A61B 5/4839 128/204.22 |
| 2010/0036272 | A1 | 2/2010 | Mace et al. |
| 2015/0283351 | A1 | 10/2015 | Castello et al. |
| 2017/0246486 | A1* | 8/2017 | Cazier .................... A61B 5/087 |
| 2017/0266399 | A1 | 9/2017 | Campana et al. |
| 2018/0078723 | A1 | 3/2018 | Caruso et al. |
| 2018/0082566 | A1 | 3/2018 | Semanoukian et al. |
| 2018/0296124 | A1 | 10/2018 | Karakaya et al. |
| 2019/0095586 | A1 | 3/2019 | McBrady et al. |
| 2019/0143071 | A1 | 5/2019 | Alrefai et al. |
| 2020/0330719 | A1 | 10/2020 | Segal et al. |
| 2021/0369995 | A1 | 12/2021 | Kuzelka |
| 2021/0379317 | A1 | 12/2021 | Cipollone et al. |
| 2022/0020488 | A1* | 1/2022 | Kennedy ................ G16H 50/20 |
| 2022/0023558 | A1 | 1/2022 | Benoit et al. |
| 2022/0296844 | A1* | 9/2022 | Gonzalez .......... A61M 16/1005 |
| 2024/0278044 | A1 | 8/2024 | Yee et al. |
| 2024/0325671 | A1 | 10/2024 | Avasthi |

FOREIGN PATENT DOCUMENTS

| | | | |
|---|---|---|---|
| EP | 3605059 | A1 | 2/2020 |
| EP | 4332568 | A1 | 3/2024 |
| KR | 10-2018-0028336 | A | 3/2018 |
| WO | 99/66304 | A1 | 12/1999 |
| WO | 2012/098303 | A1 | 7/2012 |
| WO | 2013/112287 | A1 | 8/2013 |
| WO | 2020/243369 | A1 | 12/2020 |
| WO | 2021/233957 | A1 | 11/2021 |
| WO | 2022/023958 | A1 | 2/2022 |
| WO | 2022/043664 | A2 | 3/2022 |
| WO | 2022/058967 | A1 | 3/2022 |
| WO | 2022/115899 | A1 | 6/2022 |

OTHER PUBLICATIONS

Rahul Avasthi et al., U.S. Appl. No. 18/052,666 for "Sensing and Secretion Bypass Apparatuses and Associated Methods", filed Nov. 24, 2022.

Rahul Avasthi, U.S. Appl. No. 18/194,918 for "Air Quality Analysis Device", filed Apr. 3, 2023.

Vyaire™ Respiratory consumables catalog, Vyaire, 107 pages, (2017).

Extended European Search Report Mailed on Jan. 9, 2024 for EP Application No. 23190674, 15 page(s).

Markes International, "Monitoring VOC emissions from respiratory medical devices in accordance with the new ISO 18562 international standard," Application Note 132, 1-10, (Aug. 2017).

Philips, "Philips Respironics Update on PE-PUR Testing Results and Conclusions Available to Date," 1-31, (Jun. 28, 2022).

Verena S. Aichner, "How to sample and to analyse VOCs of respiratory medical devices according to the new ISO 18562-3," Pharmind, 80(10): 1423-1427, (Nov. 2018). [Retrieved from the Internet Jan. 23, 2024: URL: <https://cdnmedia.eurofins.com/eurofins-germany/media/2848741/pi8010_1561_aichner_10-18_05nov18.pdf>].

Wojciech Wojnowski et al., "Real-time monitoring of the emission of volatile organic compounds from polylactide 3D printing filaments," Science of the Total Environment, 805(1-7), (Sep. 14, 2021).

Extended European Search Report Mailed on Apr. 9, 2024 for EP Application No. 23203471, 17 page(s).

Extended European Search Report Mailed on Jun. 26, 2024 for EP Application No. 24156150, 12 page(s).

Non-Final Rejection Mailed on Oct. 22, 2024 for U.S. Appl. No. 18/052,666, 12 page(s).

Extended European Search Report Mailed on Aug. 14, 2024 for EP Application No. 24159481, 7 page(s).

AU Office Action Mailed on Oct. 22, 2024 for AU Application No. 2024200764, 3 page(s).

* cited by examiner

AIR QUALITY MONITORING DEVICE AND ASSOCIATED METHOD OF MANUFACTURING

TECHNOLOGICAL FIELD

Embodiments of the present disclosure relate generally an air quality monitoring device and an associated method of manufacturing.

BACKGROUND

Applicant has identified many technical challenges and difficulties associated with air quality monitoring devices. Through applied effort, ingenuity, and innovation, Applicant has solved problems related to air quality monitoring devices by developing solutions embodied in the present disclosure, which are described in detail below.

BRIEF SUMMARY

Various embodiments described herein relate to an air quality monitoring device and an associated method of manufacturing.

In accordance with one aspect of the disclosure, an air quality monitoring device is provided. In some embodiments, the air quality monitoring device includes a housing having a chamber and an inlet port. In this regard, the inlet port is structured to receive an air flow from outside the housing and provide the air flow to the chamber. In some embodiments, the air quality monitoring device includes a plurality of sensors disposed within the chamber and configured to measure air quality data associated with the air flow. In some embodiments, the air quality monitoring device includes an adapter configured to be connected to the inlet port and a continuous positive airway pressure machine. In some embodiments, the inlet port is configured to receive the air flow from the continuous positive airway pressure machine via the adapter. In some embodiments, the air quality monitoring device includes a controller connected with the plurality of sensors and configured to transmit the air quality data to a computing device.

In some embodiments, the housing further includes an outlet port structured to discharge the air flow from the chamber.

In some embodiments, the plurality of sensors comprise at least one of a particulate matter sensor, a volatile organic compound sensor, a temperature sensor, or a humidity sensor.

In some embodiments, the air quality data indicates a presence of mold in the air flow based on a size of one or more particles in the air flow determined by the particulate matter sensor.

In some embodiments, the inlet port is further configured to receive ambient air flow from a surrounding environment outside the housing.

In some embodiments, the computing device determines an air quality of the air flow from the continuous positive airway pressure machine based on a comparison of the air quality data and air quality data associated with the ambient air flow from the surrounding environment outside the housing.

In some embodiments, the computing device comprises a user interface. In this regard, the user interface comprises a first interface component indicating an air quality based on the air quality data associated with a first air quality measurement and a second interface component indicating a historical air quality based on air quality data associated with a plurality of air quality measurements.

In some embodiments, the plurality of air quality measurements include the first air quality measurement.

In some embodiments, the first interface component indicates the air quality in a first color if the air quality data meets a first predetermined threshold.

In some embodiments, the adapter is interchangeable with one or more other adapters based on a type of the continuous positive airway pressure machine.

In accordance with another aspect of the disclosure, a method of manufacturing an air quality monitoring device is provided. In some embodiments, the method of manufacturing includes providing a housing comprising a chamber and an inlet port. In this regard, the inlet port is structured to receive an air flow from outside the housing and provide the air flow to the chamber. In some embodiments, the method of manufacturing includes providing a plurality of sensors disposed within the chamber and configured to measure air quality data associated with the air flow. In some embodiments, the method of manufacturing includes providing an adapter configured to be connected to the inlet port and a continuous positive airway pressure machine. In this regard, the inlet port is configured to receive the air flow from the continuous positive airway pressure machine via the adapter. In some embodiments, the method of manufacturing includes providing a controller connected with the plurality of sensors and configured to transmit the air quality data to a computing device.

In some embodiments, the housing further includes an outlet port structured to discharge the air flow from the chamber.

In some embodiments, the plurality of sensors comprise at least one of a particulate matter sensor, a volatile organic compound sensor, a temperature sensor, or a humidity sensor.

In some embodiments, the air quality data indicates a presence of mold in the air flow based on a size of one or more particles in the air flow determined by the particulate matter sensor.

In some embodiments, the inlet port is further configured to receive ambient air flow from a surrounding environment outside the housing.

In some embodiments, the computing device determines an air quality of the air flow from the continuous positive airway pressure machine based on a comparison of the air quality data and air quality data associated with the ambient air flow from the surrounding environment outside the housing.

In some embodiments, the computing device comprises a user interface. In this regard, the user interface comprises a first interface component indicating an air quality based on the air quality data associated with a first air quality measurement and a second interface component indicating a historical air quality based on air quality data associated with a plurality of air quality measurements.

In some embodiments, the plurality of air quality measurements include the first air quality measurement.

In some embodiments, the first interface component indicates the air quality in a first color if the air quality data meets a first predetermined threshold.

In some embodiments, the adapter is interchangeable with one or more other adapters based on a type of the continuous positive airway pressure machine.

The above summary is provided merely for purposes of summarizing some example embodiments to provide a basic understanding of some aspects of the present disclosure.

Accordingly, it will be appreciated that the above-described embodiments are merely examples and should not be construed to narrow the scope or spirit of the disclosure in any way. It will be appreciated that the scope of the present disclosure encompasses many potential embodiments in addition to those here summarized, some of which will be further described below.

BRIEF DESCRIPTION OF THE DRAWINGS

Reference will now be made to the accompanying drawings. The components illustrated in the figures may or may not be present in certain embodiments described herein. Some embodiments may include fewer (or more) components than those shown in the figures in accordance with an example embodiment of the present disclosure.

DETAILED DESCRIPTION

Example embodiments will be described more fully hereinafter with reference to the accompanying drawings, in which some, but not all embodiments of disclosure are shown. Indeed, embodiments of the disclosure may be embodied in many different forms and should not be construed as limited to the embodiments set forth herein; rather, these embodiments are provided so that this disclosure will satisfy applicable legal requirements. Like numbers refer to like elements throughout.

Overview

Example embodiments disclosed herein address technical problems associated with air quality monitoring devices for continuous positive airway pressure (CPAP) machines. As would be understood by one skilled in the field to which this disclosure pertains, there are numerous example scenarios in which a user may need to use an air quality monitoring device with a CPAP machine. Additionally, although the air quality monitoring device disclosed herein is referenced throughout in relation to use with a CPAP machine (a CPAP air quality monitor may also be referred to as a continuous positive airway pressure air quality (CPAQ) monitor), it would be understood by one skilled in the field to which this disclosure pertains that the air quality monitoring device may be used with any number of positive airway pressure machines such as automatic positive airway pressure (APAP) machines, bilevel positive airway pressure (BiPAP) machines, adaptive servo-ventilation (ASV) machines, and/or other mechanical ventilation machines.

Obstructive sleep apnea is a condition suffered by millions of individuals in which an individual's upper airway is obstructed while sleeping. This results in reduced breathing which causes sleep disruption and a drop in oxygen saturation. CPAP machines, in some examples, use positive pressure ventilation to apply a flow of pressurized, and in some examples heated and humified, air to an individual's upper airway while the individual sleeps to ensure the upper airway is not obstructed, thus, reducing an individual's sleep distribution and preventing a drop in oxygen saturation. In some examples, due to the frequent use of CPAP machines, materials used in the manufacturing of CPAP machines, the addition of heat and moisture to the air provided by CPAP machines, and the use of rechargeable batteries to power some CPAP machines, CPAP machines are at risk of developing and harboring inorganic particles, volatile organic compounds, toxins, and mold. As a result and in some examples, if CPAP machines are not carefully monitored to ensure their cleanliness, the flow of air provided by these machines can deliver dangerous inorganic particles, volatile organic compounds, toxins, and mold directly into an individual's upper airway. Accordingly, there is a need for devices and methods for monitoring the quality of the air that CPAP machines deliver to individuals to ensure that the air is not filled with inorganic particles, volatile organic compounds, toxins, and mold.

Thus, to address these and/or other issues related to monitoring the flow of air provided by CPAP machines, an example air quality monitoring device and an associated example method of manufacturing an air quality monitoring device are provided herein. For example, embodiments in this disclosure include an air quality monitoring device that uses a plurality of sensors within a chamber of a housing to measure air quality data associated with an air flow from a CPAP machine for particles, volatile organic compounds, and mold. The air quality data may be transmitted to a computing device which displays the air quality of the air flow on an interface in an easily digestible manner for a user of the device. Accordingly, embodiments disclosed herein enable a user of a CPAP machine to monitor the air quality of air provided by their CPAP machine to ensure that the machine is not delivering dangerous substances to the user.

Example Air Quality Monitoring Device

Figure 1:
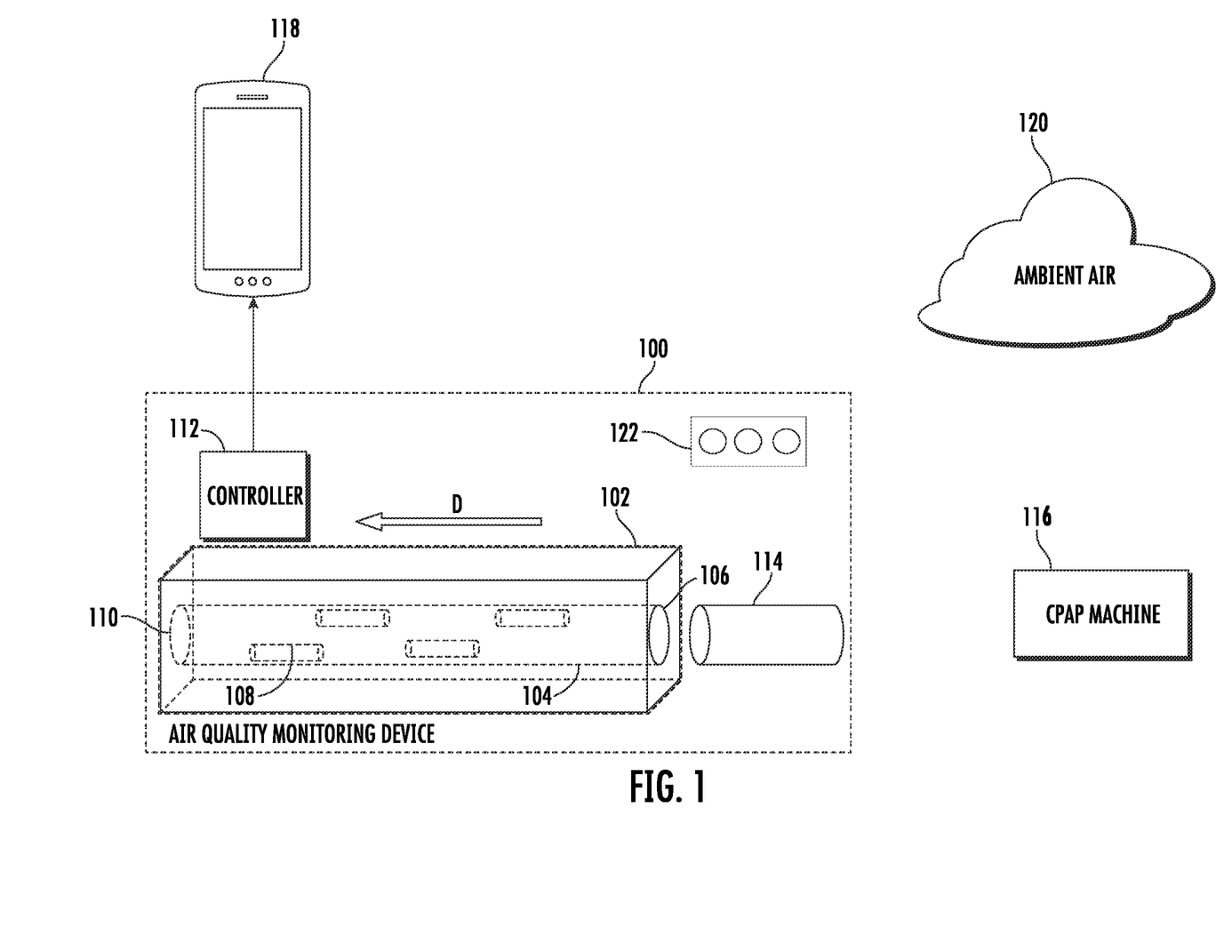
FIG. 1 illustrates an example device for performing air quality monitoring in accordance with one or more embodiments of the present disclosure.
Figure 2:
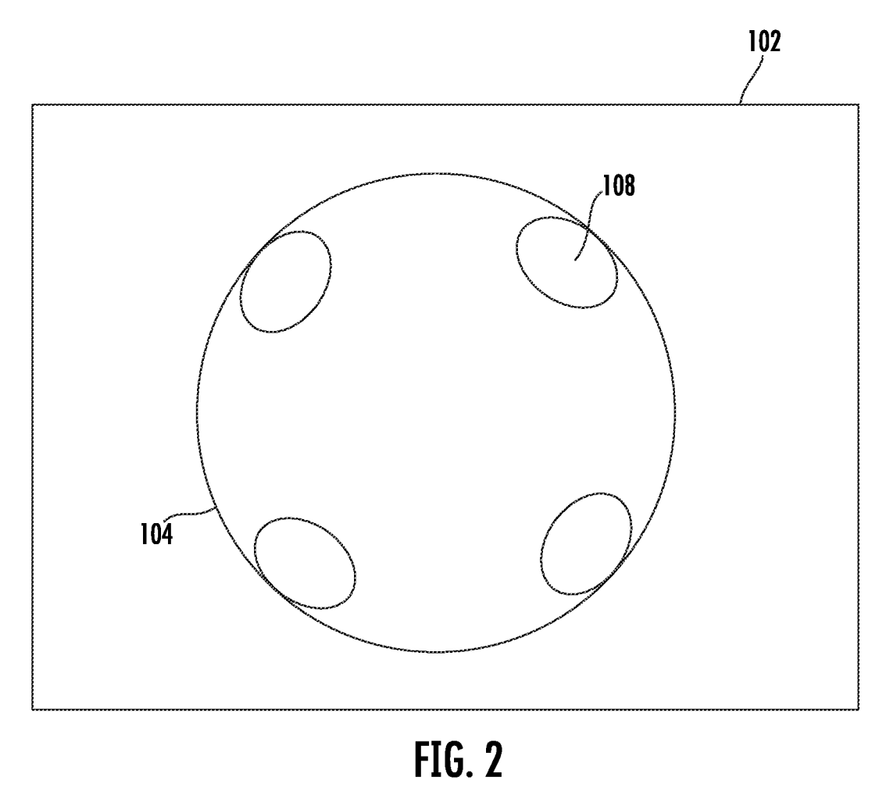
FIG. 2 illustrates an example cross-sectional view of the air quality monitoring device in accordance with one or more embodiments of the present disclosure.

With reference to FIG. 1 and FIG. 2, embodiments herein provide for an example air quality monitoring device 100. The air quality monitoring device 100 may be configured to measure an air quality of an air flow provided by a continuous positive airway pressure (CPAP) machine 116 and/or the air quality of an air flow of ambient air 120. In some embodiments, as shown in FIG. 1, the air quality monitoring device 100 may include a housing 102. The housing 102 may include a chamber 104 and an inlet port 106. The inlet port 106 is structured to receive the air flow from outside the housing and to provide the air flow to the chamber 104. In some embodiments, the air quality monitoring device 100 may include a plurality of sensors 108 disposed within the chamber 104 and configured to measure air quality data associated with the air flow.

In some embodiments, the air quality monitoring device 100 may include an adapter 114 configured to be connected to the inlet port 106 and a CPAP machine 116. In some embodiments, the inlet port may be configured to receive the air flow from the CPAP machine 116 via the adapter 114. In some embodiments, the air quality monitoring device 100 may include a controller 112 connected with the plurality of sensors 108 and configured to transmit the air quality data to a computing device 118. In some embodiments, the air quality monitoring device 100 may include an air quality indicator 122.

As described above, the air quality monitoring device 100 may include a housing 102. Although depicted as rectangular in FIGS. 1 and 2, the housing 102 may be any suitable shape. For example the housing 102 may be rectangular, square, cylindrical, spherical, triangular or any other suitable shape. In some embodiments, the housing 102 may be comprised of plastic or any other suitable material. In some embodiments, the housing 102 may be constructed using injection molding and/or 3D printing.

In some embodiments, the housing 102 of the air quality monitoring device 100 may include a chamber 104 within the housing 102. In some embodiments, the chamber 104 may be the same shape as the housing 102 (e.g., the chamber 104 may be substantially rectangular if the housing is substantially rectangular). In some embodiments, such as the depiction in FIG. 1, the chamber 104 may be a different shape than the housing 102 (e.g., the chamber 104 is substantially cylindrical while the housing 102 is substantially rectangular). In some embodiments, such as depicted in FIG. 1, the chamber 104 may be substantially straight. In some embodiments, the chamber 104 may be include bends or curves. For example, the bends or curves may enable the size of the chamber 104 to be increased without increasing the size of the housing 102.

In some embodiments, the housing 102 may further include an inlet port 106. In some embodiments, the inlet port 106 may be structured to receive an air flow from outside the housing 102 and provide the air flow to the chamber 104. In some embodiments, the air flow may be provided by the CPAP machine 116 and/or ambient air 120. In some embodiments, the housing 102 may further include an outlet port 110. The outlet port 110 may be structured to discharge the air flow from the chamber 104. In some embodiments, as depicted in FIG. 1, the air flow may travel through the chamber in direction D such that the air flow may enter the inlet port 106, travel through the chamber 104, and discharge from the chamber 104 through the outlet port 110.

In some embodiments, the air quality monitoring device 100 may include a plurality of sensors 108. The plurality of sensors 108 may be disposed within the chamber and configured to measure air quality data associated with the air flow. In some embodiments, such as depicted in FIG. 1 and FIG. 2, the plurality of sensors 108 may be disposed in different locations within the chamber 104 such that each sensor is able to measure air quality data associated with the air flow in the chamber 104 without the air flow being impacted by another one of the plurality of sensors 108. In some embodiments, the plurality of sensors 108 may be disposed along an interior surface of the chamber 104.

In some embodiments, the air quality data measured by the plurality of sensors 108 may be based on the sensors detecting particles, volatile organic compounds, and/or mold in the air flow in the chamber 104. For example, some of the plurality of sensors 108 may be configured to detect particles within a particular size range (e.g., particles between 2 µm and 20 µm) in the air flow. In this regard, the plurality of sensors 108 may include one or more particulate matter sensors. In some embodiments, the one or more particulate matter sensors may each be configured to detect particles of a specific size. For example, one particulate matter sensor may detect particles of 2 µm and another particulate matter sensor may detect particles of 10 µm. In some embodiments, some or all of the one or more particulate matter sensors may each be configured to detect multiple particles of multiple sizes and/or detect particles within a range of sizes. For example, one of the one or more particulate matter sensers may be configured to detect particles between 2 µm and 5 µm.

As another example, some of the plurality of sensors 108 may be configured to detect one or more volatile organic compounds in the air flow. In this regard, the plurality of sensors 108 may include one or more volatile organic compound sensors configured to detect volatile organic compounds, such as benzene, ethylene glycol, formaldehyde, acetone, methylene chloride, tetrachloroethylene, toluene, xylene, and/or 1,3-butadiene. In some embodiments, the one or more volatile organic compound sensors may each detect a specific volatile organic compound. For example, one volatile organic compound sensor may detect formaldehyde. In some embodiments, some or all of the one or more volatile organic compound sensors may be capable of detecting multiple volatile organic compounds.

As another example, some of the plurality of sensors 108 may be configured to detect mold in the air flow. In this regard, the plurality of sensors 108 may include one or more humidity sensors, temperature sensors, and/or, as described above, particulate matter sensors. In some embodiments, the one or more humidity sensors and temperature sensors may be used to detect the presence of mold in the air flow. For example, certain a certain humidity and/or temperature in the air flow may indicate the presence of mold. In some embodiments, the one or more particulate matter sensors may be used to detect the presence of mold in the air flow based on the size of the particles in the air flow. For example, particles with a size in the range of 4 µm and 20 µm may indicate the presence of mold.

In some embodiments, the air quality data measured by the plurality of sensors 108 may be obtained and stored in a structured and/or in an unstructured data format. For example, the air quality data may include a count of the number of times the one or more particulate matter sensors detect particles of a particular size (e.g., the one or more particulate matter sensors counted 1000 particles with a size of 10 µm in the air flow). As another example, the air quality data may include an indication of whether or not the one or more volatile organic compound sensors detect a specific volatile organic compound (e.g., the one or more volatile organic compound sensors detected formaldehyde). As another example, the air quality data may include a temperature and a humidity associated with the air flow as detected by the one or more temperature sensors and/or humidity sensors. As another example, the air quality data may include a count of the number of times the one or more particulate matter sensors detected particles of a size that indicates the presence of mold in the air flow.

In some embodiments, the air quality monitoring device 100 may include an adapter 114. The adapter 114 may be configured to be connected to the inlet port 106 and the CPAP machine 116. In some embodiments, the inlet port 106 may be configured to receive the air flow from the CPAP machine 116 via the adapter 114. In some embodiments, the adapter 114 may be configured to connect to a port of the CPAP machine 116. In some embodiments, the adapter 114 may be configured to be connected to a hose and/or tube of the CPAP machine 116. For example, the adapter 114 may be connected to a hose and/or tube of the CPAP machine 116 and the hose and/or tube of the CPAP machine 116 may be connected to a port of the CPAP machine 116. In some embodiments, the adapter 114 may be configured to be connected to a face mask of the CPAP machine 116 (e.g., the face mask may be worn by an individual suffering from obstructive sleep apnea while the individual is sleeping). For example, the adapter 114 may be connected to a face mask of the CPAP machine 116, the face mask of the CPAP machine 116 be connected to a hose and/or tube of the CPAP machine, and the hose and/or tube of the CPAP machine 116 may be connected to a port of the CPAP machine 116. In some embodiments, the adapter 114 may be interchangeable with one or more other adapters based on the type of CPAP machine. In some embodiments, the adapter 114 may be interchangeable with one or more other adapters based on whether the adapter 114 connects to a port of the CPAP machine 116, a hose and/or tube of the CPAP machine 116, and/or a face mask of the of the CPAP machine 116. Said differently, by adjusting the adapter 114, the air quality monitoring device 100 may be capable of being used with numerous different CPAP machines (e.g., CPAP machines provided by different vendors) and/or connected to various different components of a CPAP machine 116.

In some embodiments, the air quality monitoring device 100 may include a controller 112. The controller 112 may be connected with the plurality of sensors 108 and be configured to transmit the air quality data measured by the plurality of sensors 108 to a computing device 118. In some embodiments, the transmitted air quality data may be in a structured or in an unstructured format. In some embodiments, the controller 112 may transmit the air quality data measured by the plurality of sensors 108 to the computing device 118 via Wi-Fi and/or Bluetooth. In some embodiments, the controller 112 may be configured to transmit the air quality data to the computing device in real-time. For example, each time one of the one or more volatile organic compound sensors detects a volatile organic compound, the controller 112 may transmit air quality data associated with the detection of the volatile organic compound to the computing device 118.

In some embodiments, the controller 112 may be configured to transmit the air quality data to the computing device 118 on a pre-determined schedule. For example, the controller 112 may transmit the air quality data to the computing device 118 every 20 seconds. In some embodiments, the controller 112 may be configured to transmit the air quality data to the computing device 118 at the end of a monitoring period. For example, the controller 112 may be configured to identify when air flow has started flowing through the chamber 104 and when air flow has stopped flowing through the chamber 104. In this regard, when the controller 112 has identified that the air flow has stopped flowing through the chamber 104, the controller 112 may transmit the air quality data to the computing device 118. In some embodiments, the controller 112 may be configured to transmit the air quality data to the computing device 118 upon receiving an instruction to transmit the air quality data from the computing device 118.

In some embodiments, the computing device 118 may receive the air quality data from the controller 112. In some embodiments, the air quality data the computing device 118 receives from the controller 112 may be in a structured or in an unstructured format. In some embodiments, the computing device 118 may use the unstructured air quality data to generate an air quality associated with the air flow measured by the plurality of sensors 108. In this regard, a user of the computing device 118 may be able to determine the air quality of the air flow provided by the CPAP machine 116 or the air flow of the ambient air 120.

Although described herein with respect to the computing device 118 receiving the air quality data from the controller 112 and generating the air quality associated with the air flow measured by the plurality of sensors 108, it would be understood by one skilled in the field to which this disclosure pertains that, in some embodiments, the controller 112 may be configured to use the unstructured air quality data to generate an air quality associated with the air flow measured by the plurality of sensors 108. Additionally, it would be understood by one skilled in the field to which this disclosure pertains that, in such embodiments, the controller 112 may be configured to transmit the generated air quality to the computing device 118 (e.g., via Wi-Fi or Bluetooth).

In some embodiments, the air quality generated by the computing device 118 may be based on the air quality data measured by the one or more particulate sensors of the plurality of sensors 108. For example, if the air quality data indicates that the count of the number of times the one or more particulate matter sensors detect particles of a particular size in the air flow is less than a first particle threshold, the computing device 118 may determine that the air quality is good. If the air quality data indicates that the count of the number of times the one or more particulate matter sensors detect particles in the air flow of a particular size is greater than the first particle threshold but less than a second particle threshold, the computing device 118 may determine that the air quality is moderate. If the air quality data indicates that the count of the number of times the one or more particulate matter sensors detect particles of a particular size in the air flow is greater than the second particle threshold, the computing device 118 may determine that the air quality is bad. In some embodiments, the count of the number of times the one or more particulate matter sensors detect particles of a particular size may be done within a predefined time limit. (e.g., how many particles of a particular size are counted within one hour). In some embodiments, the first threshold and the second threshold may be based on the Air Quality Index (AQI) set by the United States Environmental Protection Agency.

In some embodiments, the air quality determined by the computing device 118 may be based on air quality data measured by the one or more volatile organic compound sensors of the plurality of sensors 108. For example, in some embodiments, if the air quality data indicates that the one or more volatile organic compound sensors have detected a volatile organic compound in the air flow, the computing device 118 may determine that the air quality is bad or moderate. In some embodiments, if the air quality data indicates that the one or more volatile organic compound sensors have not detected a volatile organic compound in the air flow, the computing device may determine that the air quality is good. In some embodiments, if the air quality data indicates that the one or more volatile organic compound sensors have detected a volatile organic compound in the air flow, the computing device 118 may determine whether the air quality is good, moderate, or bad based on the specific type of volatile organic compound in the air flow. In some embodiments, if the air quality data indicates that the one or more volatile organic compound sensors have detected multiple volatile organic compounds in the air flow, the computing device may determine if the air quality is good, moderate, or bad, based on the quantity of volatile organic compounds in the air flow and/or the specific types of volatile organic compounds in the air flow.

In some embodiments, the air quality determined by the computing device 118 may be based on air quality data measured by the one or more temperature sensors, humidity sensors, and/or particulate matter sensors of the plurality of sensors 108 that indicate the presence of mold in the air flow. For example, in some embodiments, if the air quality data indicates that the temperature is above a first temperature threshold and/or the humidity is above a first humidity threshold, the computing device 118 may determine that there is mold present in the air flow and that the air quality is bad or moderate. In some embodiments, if the air quality indicates that the temperature is below the first temperature threshold and/or the humidity is below the first humidity threshold, the computing device 118 may determine that mold is not present in the air flow and that the air quality is moderate or good. In some embodiments, if the air quality data indicates that the one or more particulate matter sensors detect particles of a particular size in the air flow, the computing device 118 may determine that there is mold present in the air flow and that the air quality is bad or moderate. In some embodiments, if the air quality data indicates that the one or more particulate matter sensors do not detect particles of a particular size in the air flow, the computing device 118 may determine that mold is not present in the air flow and that the air quality is moderate or good.

In some embodiments, the air quality determined by the computing device 118 may be based on air quality data measured by a combination of some or all of the different sensors in the plurality of sensors 108. For example, in some embodiments, the computing device 118 may determine that the air quality is good if the air quality data indicates that the count of the number of times the one or more particulate matter sensors detect particles of a particular size in the air flow is less than the first particle threshold, the one or more volatile organic compound sensors have not detected a volatile organic compound in the air flow, and mold is not present in the air flow. In some embodiments, the computing device 118 may determine that the air quality is moderate if the air quality data indicates that the count of the number of times the one or more particulate matter sensors detect particles of a particular size in the air flow is greater than the second particle threshold, the one or more volatile organic compound sensors detected a volatile organic compound in the air flow, or mold is present in the air flow. In some embodiments, the computing device 118 may determine that the air quality is bad if the air quality data indicates that the count of the number of times the one or more particulate matter sensors detect particles of a particular size in the air flow is greater than the second particle threshold, the one or more volatile organic compound sensors detected a volatile organic compound in the air flow, and mold is present in the air flow.

In some embodiments, the computing device 118 may compare air quality data associated with air flow provided by the CPAP machine 116 against air quality data associated with ambient air flow provided by ambient air 120. In some embodiments, the computing device 118 may use the comparison of the air quality data associated with air flow provided by the CPAP machine 116 against air quality data associated with ambient air flow provided by ambient air 120, to determine the air quality of the air flow provided by the CPAP machine 116. In this regard, since, as described above, the CPAP machine 116 may take in ambient air, filter the ambient air, pressurize the filtered ambient air, and then provide it to the inlet port 106 via the adapter 114, the computing device may be able to precisely determine factors affecting the air quality that are caused by the CPAP machine 116. Said differently, if the air quality data associated with the ambient air flow indicates that the one or more volatile organic compound sensors did not detect a volatile organic compound while the air quality data associated with the air flow provided by the CPAP machine 116 indicates that the one or more volatile organic compound sensors did detect a volatile organic compound, the computing device 118 may determine that the CPAP machine 116 is the source of the detected volatile organic compound.

In some embodiments, the air quality data associated with the air flow provided by the CPAP machine 116 may be from a first air quality measurement when the air quality monitoring device 100 was connected to the CPAP machine 116 and the air quality data associated with the air flow provided by ambient air 120 may be from a second air quality measurement when the air quality monitoring device 100 was not connected to the CPAP machine 116 (e.g., during the second air quality measurement the adapter 114 was not connected to the inlet port 106). In some embodiments, the computing device 118 may only compare the air quality data associated with air flow provided by the CPAP machine 116 against air quality data associated with ambient air flow provided by ambient air 120 when the first air quality measurement and the second air quality measurement both occurred within a predefined time period (e.g., the first air quality measurement and the second air quality measurement occurred within five minutes of each other).

In some embodiments, the computing device 118 may store determined air quality and associated air quality data in memory, such that the computing device 118 may be able to generate a historical air quality and historical air quality data. In this regard, the computing device may be able to associate air quality data received from the controller 112 and a determined air quality with an air quality measurement. In some embodiments, the computing device 118 may be configured to compile air quality data and air quality from multiple air quality measurements into a plurality of air quality measurements to generate historical air quality and historical air quality data. Accordingly, the historical air quality may represent the air quality determined by the computing device 118 over a period of time through multiple air quality tests. In some embodiments, this may help a user of the computing device 118 and/or the air quality monitoring device 100 track air quality trends associated with the CPAP machine 116 and/or the ambient air 120.

Figure 3:
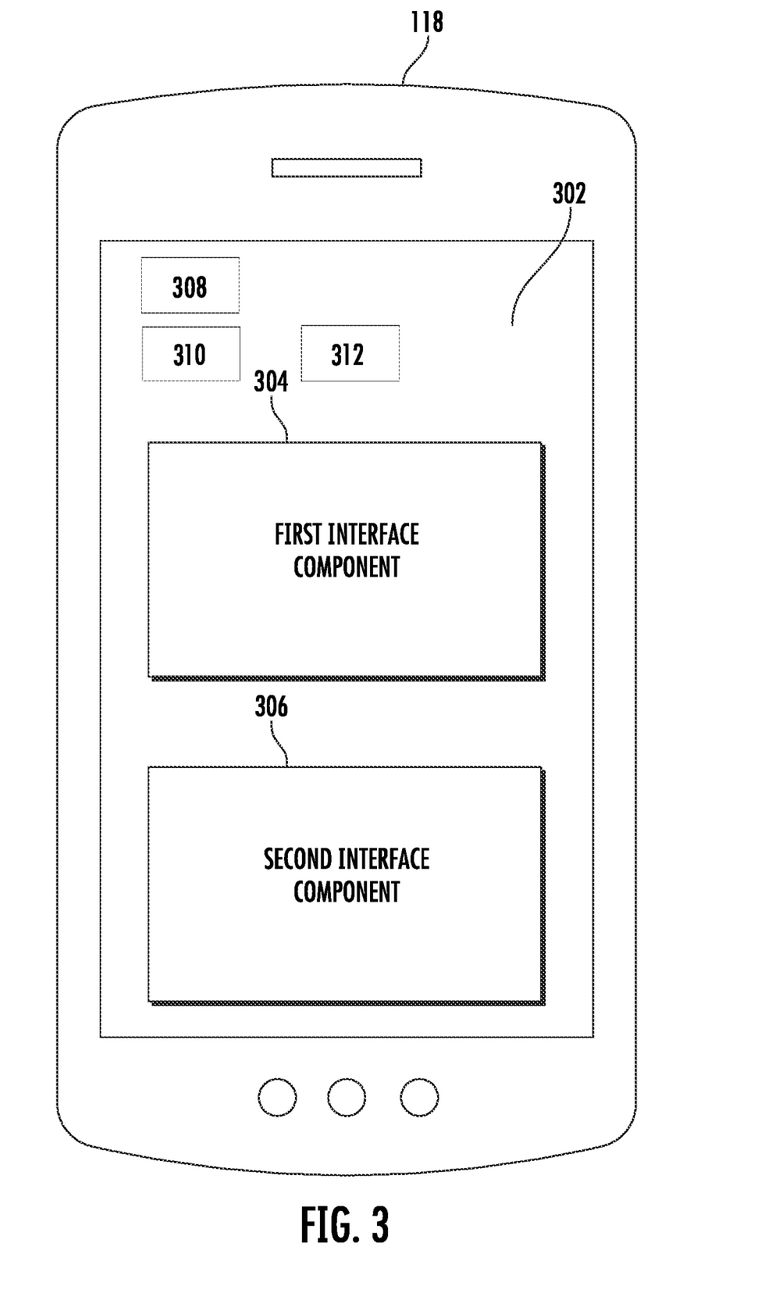
FIG. 3 illustrates an example user interface of a computing device in accordance with one or more embodiments of the present disclosure.

With reference to FIG. 3, in some embodiments, the computing device 118 may include a user interface 302. In some embodiments, the user interface 302 may be provided by a mobile application executing on the computing device 118. In some embodiments, the user interface 302 may include a first interface component 304 and a second interface component 306. In some embodiments, the first interface component 304 may indicate an air quality and/or air quality data associated with a first air quality measurement. In some embodiments, the first air quality measurement may be the most recent air quality measurement performed air quality measurement (e.g., the most recent air quality data received from the controller 112 and air quality determined by the computing device 118). In some embodiments, the second interface component 306 may indicate the historical air quality and/or historical air quality data based on a plurality of air quality measurements. In some embodiments, the plurality of air quality measurements may include the first air quality measurement.

In some embodiments, the first interface component 304 and the second interface component 306 may include charts, graphs, text, colors, and/or the like that indicate the air quality, air quality data, historical air quality, and/or historical air quality data. For example, if the air quality is good, the first interface component 304 may include green coloring. As another example, if the historical air quality is trending downwards, the second interface component 306 may include red coloring. As another example, the first interface component 304 and/or the second interface component 306 may include text that indicates the air quality data and/or the historical air quality data (e.g., text may indicate a particular volatile organic compound).

In some embodiments, the user interface 302 may include a first selectable component 308. In some embodiments, a user may use the first selectable component 308 to adjust the historical air quality and/or historical air quality data displayed on the second interface component 306. For example, a user may use the first selectable component 306 to cause the second interface component 306 to display the ten most recent air quality measurements in the plurality of air quality measurements. In some embodiments, the user interface 302 may include a second selectable component 310. In some embodiments, a user may use the second selectable component 310 to download the air quality, air quality data, historical air quality, and/or historical air quality data. In some embodiments, the air quality, air quality data, historical air quality, and/or historical air quality data may be download in pdf format, spreadsheet format, and/or any other suitable format for downloading. In some embodiments, the user interface 302 may include a third selectable component 312. In some embodiments, a user may use the third selectable component 312 to share the air quality, air quality data, historical air quality, and/or historical air quality data. In some embodiments, the air quality, air quality data, historical air quality, and/or historical air quality data may be shared via email, text message, social media post, and/or any other suitable method of sharing.

Referring again to FIG. 1, as described above the air quality monitoring device 100 may include an air quality indicator 122. In some embodiments, the air quality indicator 122 may be configured to indicate the air quality associated with an air quality measurement. In some embodiments, the air quality indicator 122 may use colors, numbers, text, and/or the like to indicate the air quality associated with an air quality measurement (e.g., the air quality indicator 122 may include a green light, a yellow light, and a red light). For example, if the air quality associated with an air quality measurement is good, the air quality indicator 122 may be configured to show a green light. As another example, if the air quality associated with the air quality measurement is bad, the air quality indicator 122 may be configured to show a red light. In some embodiments, such as when the computing device 118 generates the air quality, the controller 112 may receive the air quality from the computing device 118 and cause the air quality indicator 122 to indicate the air quality. In some embodiments, such as when the controller 112 generates the air quality, the controller 112 may cause the air quality indicator 122 to indicate the air quality.

Example Computer Processing Device

Figure 4:
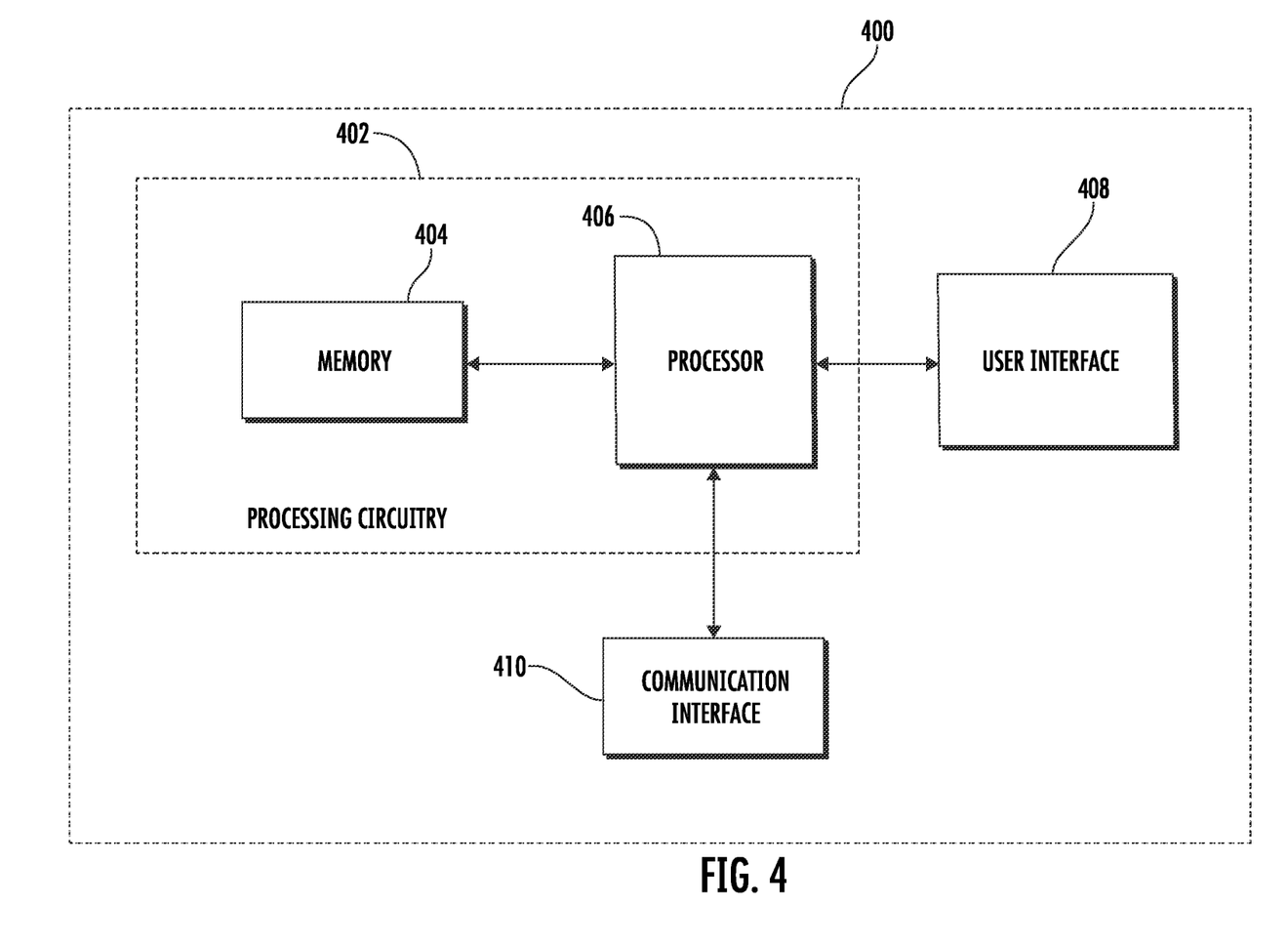
FIG. 4 illustrates a block diagram of an example computing device in accordance with one or more embodiments of the present disclosure.

With reference to FIG. 4, a block diagram of an example computer processing device 400 is illustrated in accordance with some example embodiments. In some embodiments, the computing device 118 and/or the controller 112 may be embodied as one or more computer processing devices, such as the computer processing device 400 in FIG. 4. However, it should be noted that the components, devices, or elements illustrated in and described with respect to FIG. 4 below may not be mandatory and thus one or more may be omitted in certain embodiments. Additionally, some embodiments may include further or different components, devices or elements beyond those illustrated in and described with respect to FIG. 4.

The computer processing device 400 may include or otherwise be in communication with processing circuitry 402 that is configurable to perform actions in accordance with one or more embodiments disclosed herein. In this regard, the processing circuitry 402 may be configured to perform and/or control performance of one or more functionalities of the computer processing device 400 in accordance with various embodiments, and thus may provide means for performing functionalities of the computer processing device 400 in accordance with various embodiments. The processing circuitry 402 may be configured to perform data processing, application execution and/or other processing and management services according to one or more embodiments. In some embodiments, the computer processing device 400 or a portion(s) or component(s) thereof, such as the processing circuitry 402, may be embodied as or comprise a chip or chip set. In other words, the computer processing device 400 or the processing circuitry 402 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The computer processing device 400 or the processing circuitry 402 may therefore, in some cases, be configured to implement an embodiment of the disclosure on a single chip or as a single "system on a chip." As such, in some cases, a chip or chipset may constitute means for performing one or more operations for providing the functionalities described herein.

In some embodiments, the processing circuitry 402 may include a processor 406 and, in some embodiments, such as that illustrated in FIG. 4, may further include memory 404. The processing circuitry 402 may be in communication with or otherwise control a user interface 408 and/or a communication interface 410. As such, the processing circuitry 402 may be embodied as a circuit chip (e.g., an integrated circuit chip) configured (e.g., with hardware, software or a combination of hardware and software) to perform operations described herein.

The processor 406 may be embodied in a number of different ways. For example, the processor 406 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor 406 may comprise a plurality of processors. The plurality of processors may be in operative communication with each other and may be collectively configured to perform one or more functionalities of the computer processing device 400 as described herein. In some embodiments, the processor 406 may be configured to execute instructions stored in the memory 404 or otherwise accessible to the processor 406. As such, whether configured by hardware or by a combination of hardware and software, the processor 406 may represent an entity (e.g., physically embodied in circuitry—in the form of processing circuitry 402) capable of performing operations according to embodiments of the present disclosure while configured accordingly. Thus, for example, when the processor 406 is embodied as an ASIC, FPGA or the like, the processor 406 may be specifically configured hardware for conducting the operations described herein. Alternatively, as another example, when the processor 406 is embodied as an executor of software instructions, the instructions may specifically configure the processor 406 to perform one or more operations described herein.

In some embodiments, the memory 404 may include one or more non-transitory memory devices such as, for example, volatile and/or non-volatile memory that may be either fixed or removable. In this regard, the memory 404 may comprise a non-transitory computer-readable storage medium. It will be appreciated that while the memory 404 is illustrated as a single memory, the memory 404 may comprise a plurality of memories. The memory 404 may be configured to store information, data, applications, instructions and/or the like for enabling the computer processing device 400 to carry out various functions in accordance with one or more embodiments. For example, the memory 404 may be configured to buffer input data for processing by the processor 406. Additionally or alternatively, the memory 404 may be configured to store instructions for execution by the processor 406. As yet another alternative, the memory 404 may include one or more databases that may store a variety of files, contents or data sets. Among the contents of the memory 404, applications may be stored for execution by the processor 406 in order to carry out the functionality associated with each respective application. In some cases, the memory 404 may be in communication with one or more of the processor 406, user interface 408, and/or communication interface 410 via a bus(es) for passing information among components of the computer processing device 400.

The user interface 408 may be in communication with the processing circuitry 402 to receive an indication of a user input at the user interface 408 and/or to provide an audible, visual, mechanical or other output to the user. As such, the user interface 408 may include, for example, a keyboard, a mouse, a joystick, a display, a touch screen display, a microphone, a speaker, and/or other input/output mechanisms. As such, the user interface 408 may, in some embodiments, provide means for a user to access and interact with the computing device 118 and/or the air quality monitoring device 100.

The communication interface 410 may include one or more interface mechanisms for enabling communication with other devices and/or networks. In some cases, the communication interface 410 may be any means such as a device or circuitry embodied in either hardware, or a combination of hardware and software that is configured to receive and/or transmit data from/to a network and/or any other device or module in communication with the processing circuitry 402. By way of example, the communication interface 410 may be configured to enable the computing device 118 and/or the controller 112 to communicate with each other and/or other computer processing devices. Accordingly, the communication interface 410 may, for example, include an antenna (or multiple antennas) and supporting hardware and/or software for enabling communications with a wireless communication network (e.g., a wireless local area network, cellular network, global positioning system network, and/or the like) and/or a communication modem or other hardware/software for supporting communication via cable, digital subscriber line (DSL), universal serial bus (USB), Ethernet or other methods.

Example Method of Manufacturing an Air Quality Monitoring Device

Figure 5:
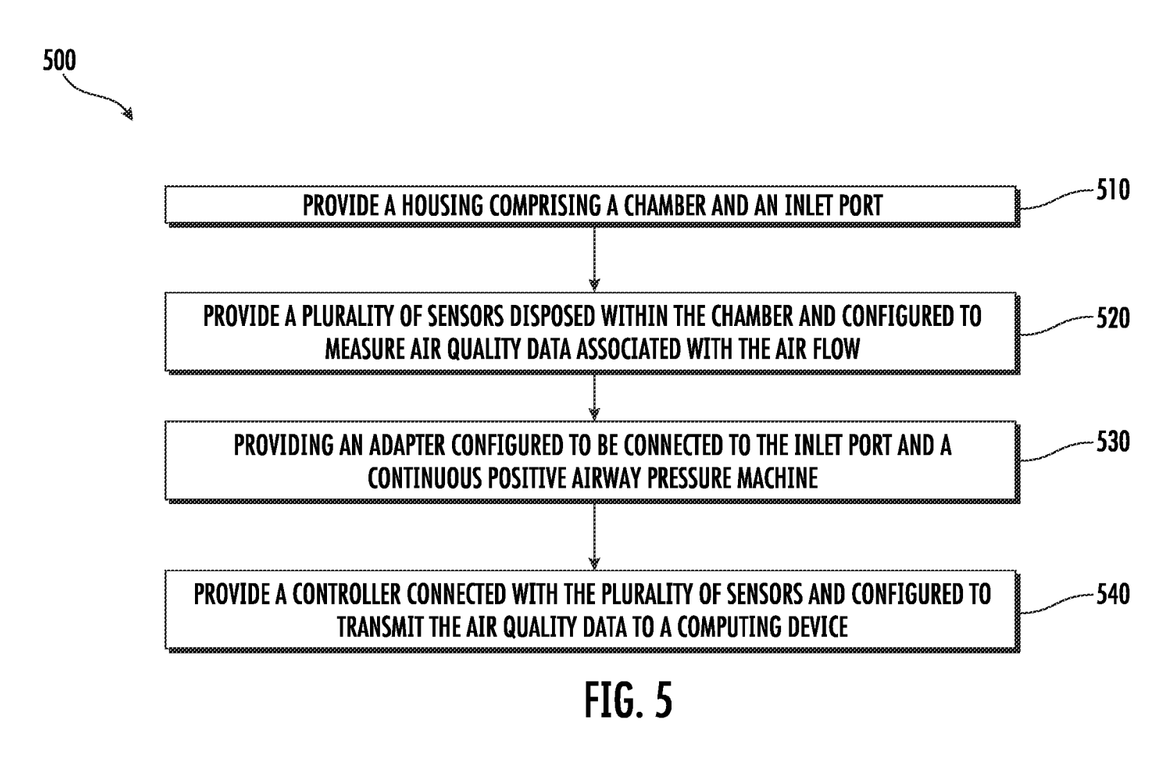
FIG. 5 illustrates a flow chart of an example method of manufacturing an air quality monitoring device in accordance with one or more embodiments of the present disclosure.

Referring now to FIG. 5, a flowchart providing an example method 500 for manufacturing an air quality monitoring device is illustrated.

As shown in block 510, the method of manufacturing may include providing a housing having a chamber and an inlet port. As described above, the inlet port may be structured to receive an air flow from outside the housing and provide the air flow to the chamber. In some embodiments, the housing may further include an outlet port structured to discharge the air flow from the chamber.

As shown in block 520, the method of manufacturing may include providing a plurality of sensors disposed within the chamber and configured to measure air quality data associated with the air flow. As described above, the plurality of sensors disposed within the chamber may include one or more particulate matter sensors, one or more volatile organic compound sensors, one or more temperature sensors, and/or one or more humidity sensors. As described above, the air quality data indicates a presence of mold in the air flow based on a size of one or more particles in the air flow determined by the particulate matter sensor.

As shown in block 530, the method of manufacturing may include providing an adapter configured to be connected to the inlet port and a continuous positive airway pressure machine. As described above, the inlet port may be configured to receive the air flow from the continuous positive airway pressure machine via the adapter. In some embodiments, the inlet port may be further configured to receive ambient air flow from ambient air from a surrounding environment outside the housing. In some embodiments, the adapter may be interchangeable with one or more other adapters based on a type of the continuous positive airway pressure machine.

As shown in block 540, the method of manufacturing may include providing a controller connected with the plurality of sensors and configured to transmit the air quality data to a computing device. As described above, the computing device may determine an air quality of the air flow from the continuous positive airway pressure machine based on a comparison of the air quality data and air quality data associated with the ambient air flow from the surrounding environment outside the housing. As described above, the computing device may include a user interface. The user interface may include a first interface component indicating an air quality based on the air quality data associated with a first air quality measurement and a second interface component indicating a historical air quality based on air quality data associated with a plurality of air quality measurements. In some embodiments, the plurality of air quality measurements include the first air quality measurement. In some embodiments, the first interface component indicates the air quality in a first color if the air quality data meets a first predetermined threshold.

Example Method of Performing Air Quality Monitoring

Figure 6:
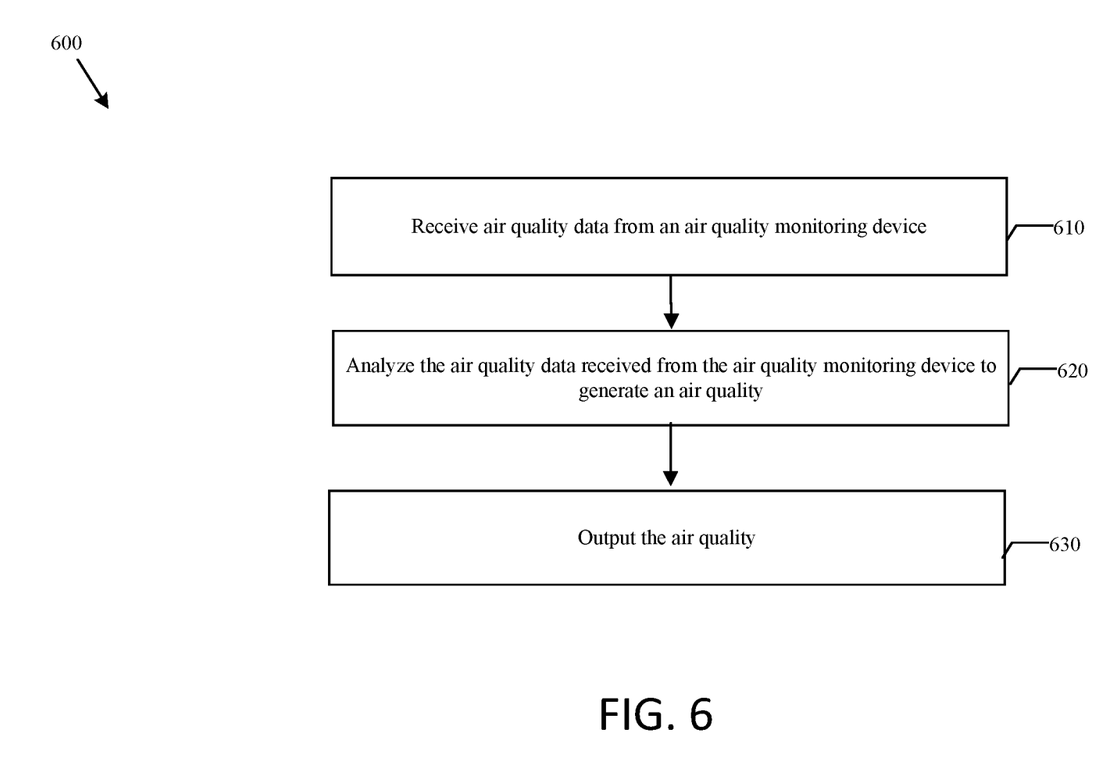
FIG. 6 illustrates a flow chart of an example method of performing air quality monitoring in accordance with one or more embodiments of the present disclosure.

Referring now to FIG. 6, a flowchart providing an example method 600 for performing air quality monitoring is illustrated. In some embodiments, the operations illustrated in FIG. 6 may, for example, be perform by, with the assistance of, and/or under the control of a computer processing device (e.g., the computer processing device 400). In this regard, performance of the operations may invoke one or more of processor 406, memory 404, processing circuitry 402, communication interface 410, and/or the user interface 408.

As shown in block 610, the method may include receiving air quality data from an air quality monitoring device (e.g., the air quality monitoring device described above). As shown in block 620, the method may include analyzing the air quality data received from the air quality monitoring device to generate an air quality. In this regard, the analysis of the air quality data to generate the air quality may include the analysis of the air quality data described above. For example, the analysis may include determining that the air quality is bad or moderate if one or more volatile organic compound sensors of the air quality monitoring device detect a volatile organic compound in an air flow associated with the air quality data. As shown in block 630, the method may include outputting the air quality. For example, the air quality may be outputted to the user interface of the air quality monitoring device as described above.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

That which is claimed:

1. An air quality monitoring device, the air quality monitoring device comprising:
    a housing comprising a chamber and an inlet port, wherein the inlet port is structured to receive an air flow from outside the housing and provide the air flow to the chamber, wherein the inlet port is further configured to receive ambient air flow from a surrounding environment outside the housing;
    a plurality of sensors disposed within the chamber and configured to measure air quality data associated with the air flow;
    an adapter configured to be connected to the inlet port and a continuous positive airway pressure machine, wherein the inlet port is configured to receive the air flow from the continuous positive airway pressure machine via the adapter;
    a controller connected with the plurality of sensors and configured to transmit the air quality data to a computing device, wherein the computing device determines an air quality of the air flow from the continuous positive airway pressure machine based on a comparison of the air quality data and air quality data associated with the ambient air flow from the surrounding environment outside the housing; and
    wherein the computing device comprises a user interface, wherein the user interface comprises a first interface component indicating an air quality based on the air quality data associated with a first air quality measurement and a second interface component indicating a historical air quality based on air quality data associated with a plurality of air quality measurements.

2. The air quality monitoring device of claim 1, wherein the housing further comprises:
    an outlet port structured to discharge the air flow from the chamber.

3. The air quality monitoring device of claim 1, wherein the plurality of sensors comprise at least one of a particulate matter sensor, a volatile organic compound sensor, a temperature sensor, or a humidity sensor.

4. The air quality monitoring device of claim 3, wherein the air quality data indicates a presence of mold in the air flow based on a size of one or more particles in the air flow determined by the particulate matter sensor.

5. The air quality monitoring device of claim 1, wherein the plurality of air quality measurements include the first air quality measurement.

6. The air quality monitoring device of claim 1, wherein the first interface component indicates the air quality in a first color if the air quality data meets a first predetermined threshold.

7. The air quality monitoring device of claim 1, wherein the adapter is interchangeable with one or more other adapters based on a type of the continuous positive airway pressure machine.

8. A method of manufacturing an air quality monitoring device, the method comprising:
    providing a housing comprising a chamber and an inlet port, wherein the inlet port is structured to receive an air flow from outside the housing and provide the air flow to the chamber, wherein the inlet port is further configured to receive ambient air flow from a surrounding environment outside the housing;
    providing a plurality of sensors disposed within the chamber and configured to measure air quality data associated with the air flow;
    providing an adapter configured to be connected to the inlet port and a continuous positive airway pressure machine, wherein the inlet port is configured to receive the air flow from the continuous positive airway pressure machine via the adapter;
    providing a controller connected with the plurality of sensors and configured to transmit the air quality data to a computing device, wherein the computing device determines an air quality of the air flow from the continuous positive airway pressure machine based on a comparison of the air quality data and air quality data associated with the ambient air flow from the surrounding environment outside the housing; and
    wherein the computing device comprises a user interface, wherein the user interface comprises a first interface component indicating an air quality based on the air quality data associated with a first air quality measurement and a second interface component indicating a historical air quality based on air quality data associated with a plurality of air quality measurements.

9. The method of manufacturing an air quality monitoring device of claim 8, wherein the housing further comprises:
   an outlet port structured to discharge the air flow from the chamber.

10. The method of manufacturing an air quality monitoring device of claim 8, wherein the plurality of sensors comprise at least one of a particulate matter sensor, a volatile organic compound sensor, a temperature sensor, or a humidity sensor.

11. The method of manufacturing an air quality monitoring device of claim 10, wherein the air quality data indicates a presence of mold in the air flow based on a size of one or more particles in the air flow determined by the particulate matter sensor.

12. The method of manufacturing an air quality monitoring device of claim 8, wherein the plurality of air quality measurements include the first air quality measurement.

13. The method of manufacturing an air quality monitoring device of claim 8, wherein the first interface component indicates the air quality in a first color if the air quality data meets a first predetermined threshold.

14. The method of manufacturing an air quality monitoring device of claim 8, wherein the adapter is interchangeable with one or more other adapters based on a type of the continuous positive airway pressure machine.

* * * * *